United States Patent
Barry

(10) Patent No.: US 6,632,230 B2
(45) Date of Patent: Oct. 14, 2003

(54) ABLATION SYSTEM WITH CATHETER CLEARING ABRASIVE

(75) Inventor: Robert L. Barry, Kirkland, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/835,130

(22) Filed: Apr. 12, 2001

(65) Prior Publication Data

US 2002/0151917 A1 Oct. 17, 2002

(51) Int. Cl.[7] .............................................. A61B 17/22
(52) U.S. Cl. ....................................... 606/159; 604/46
(58) Field of Search ....................... 606/1, 108, 159, 606/170, 171, 180; 604/22

(56) References Cited

U.S. PATENT DOCUMENTS

| | | | | |
|---|---|---|---|---|
| 4,732,154 A | * | 3/1988 | Shiber | 606/108 |
| 5,154,724 A | * | 10/1992 | Andrews | 604/22 |
| 5,318,576 A | * | 6/1994 | Plassche et al. | 604/22 |
| 5,507,732 A | * | 4/1996 | McClure et al. | 604/256 |
| 5,569,275 A | | 10/1996 | Kotula et al. | |
| 5,681,336 A | * | 10/1997 | Clement et al. | 606/159 |
| 5,766,192 A | * | 6/1998 | Zacca | 606/159 |
| 5,772,627 A | * | 6/1998 | Acosta et al. | 604/22 |
| 5,779,721 A | | 7/1998 | Nash | |
| 5,843,103 A | * | 12/1998 | Wulfman | 606/159 |
| 6,001,112 A | * | 12/1999 | Taylor | 606/159 |
| 6,074,357 A | * | 6/2000 | Kaganov et al. | 604/8 |
| 6,129,698 A | | 10/2000 | Beck | |
| 6,146,395 A | * | 11/2000 | Kanz et al. | 606/159 |
| 6,152,913 A | * | 11/2000 | Feith et al. | 604/533 |
| 6,183,487 B1 | | 2/2001 | Barry et al. | |
| 6,344,049 B1 | * | 2/2002 | Levinson et al. | 600/585 |
| 6,451,036 B1 | * | 9/2002 | Heitzmann et al. | 606/159 |

* cited by examiner

*Primary Examiner*—Michael J. Milano
*Assistant Examiner*—Victor X Nguyen
(74) *Attorney, Agent, or Firm*—Christensen O'Connor Johnson Kindness PLLC

(57) ABSTRACT

An ablation system comprising an atherectomy device and an aspiration catheter, each routed to a position just proximal to a lesion within a patient's vessel to ablate the lesion. The atherectomy device includes a flexible driveshaft coupled to an ablation burr. The ablation burr includes a concave front surface and a generally frusto-conical rear surface, both having an abrasive disposed thereon. The aspiration catheter has an elongate body and includes a centrally located lumen. The distal portion of the lumen is frusto-conical in shape and is positioned at the distal end of the catheter to define an aspiration mouth. The taper of the frusto-conical portion of the lumen corresponds to the taper of the rear surface of the ablation burr so that the ablation burr may be pulled back into the distal portion of the lumen of the catheter during operation of the system to clear captured ablated material therein.

7 Claims, 3 Drawing Sheets

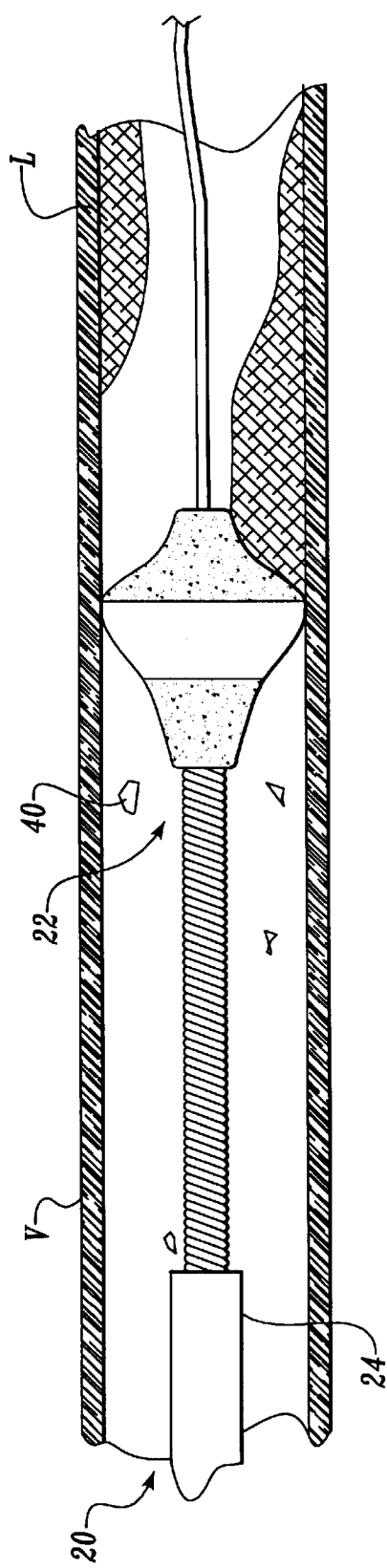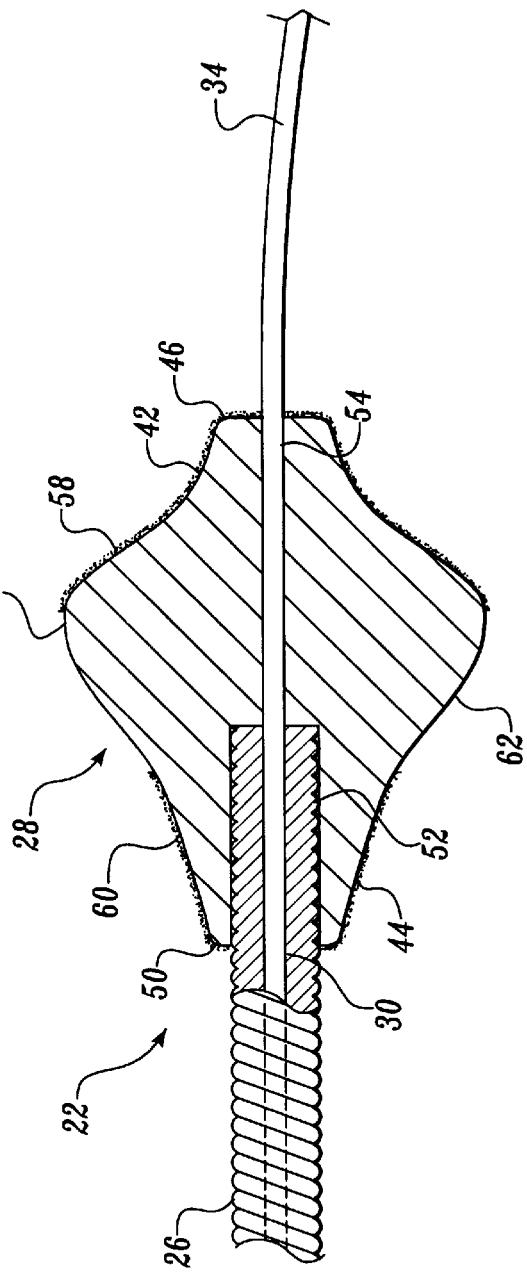

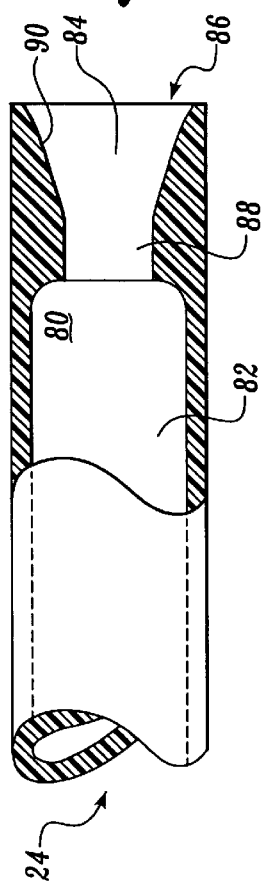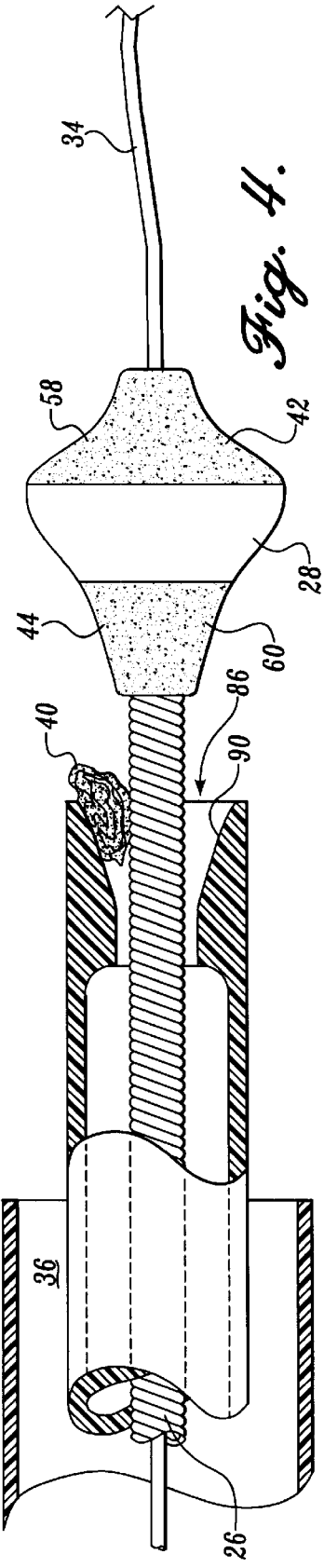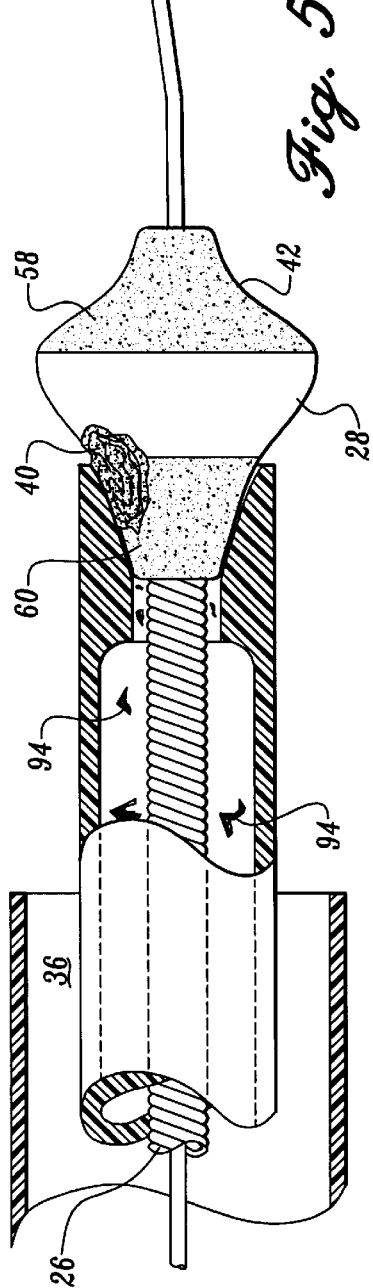

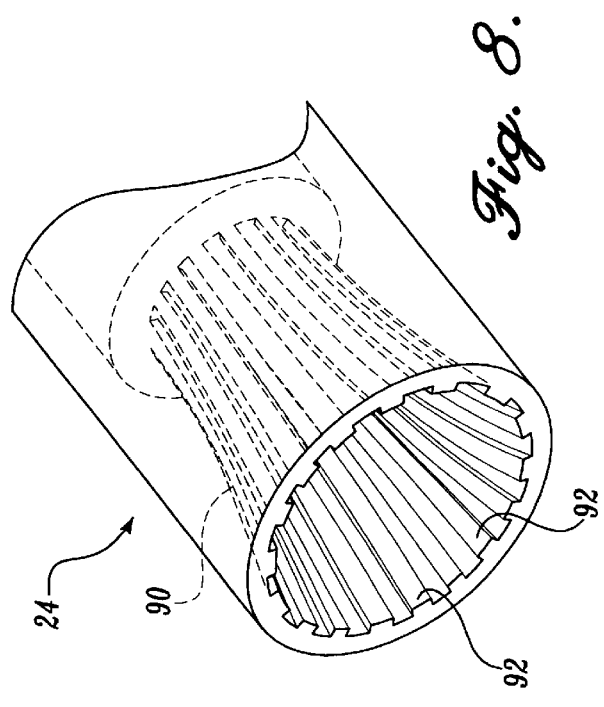
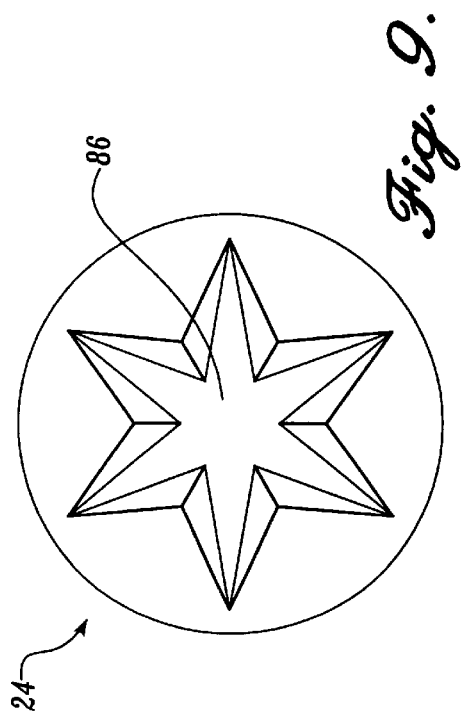
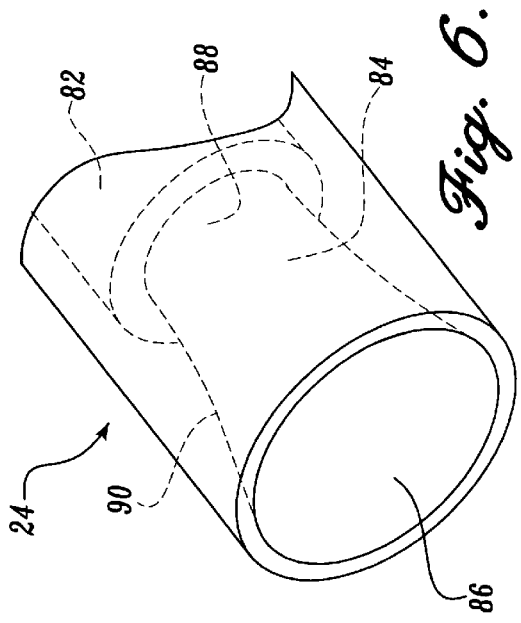
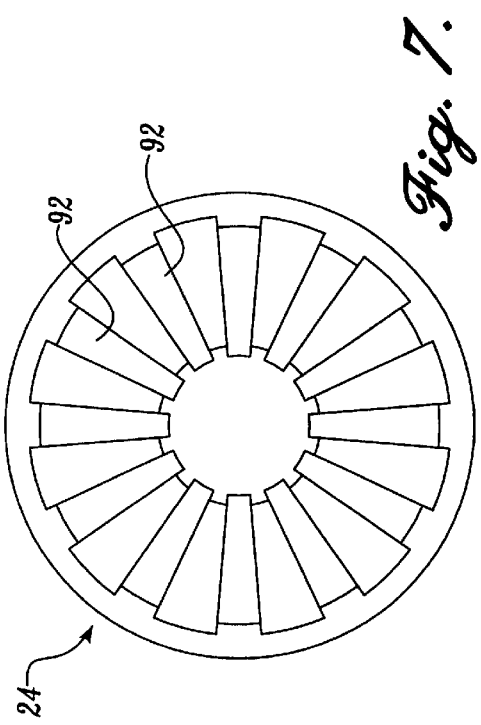

ABLATION SYSTEM WITH CATHETER CLEARING ABRASIVE

FIELD OF THE INVENTION

The present invention generally relates to devices for removing undesirable deposits from the lumen of a blood vessel or from a stent positioned within a blood vessel, and more particularly, to atherectomy devices.

BACKGROUND OF THE INVENTION

Vascular diseases, such as atherosclerosis and the like, have become quite prevalent in the modern day. These diseases may present themselves in a number of forms. Each form of vascular disease may require a different method of treatment to reduce or cure the harmful effects of the disease. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of invasive therapies are available, it is desirable to develop noninvasive therapies as well. Non-invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots, which may be blocking a particular vascular lumen. Other drug therapies are also available. Further non-invasive, intravascular treatments exist that are not only pharmaceutical, but also revascularize blood vessels or lumens by mechanical means. Two examples of such intravascular therapies are balloon angioplasty and atherectomy that physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member that is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but displaces and reforms it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

A relatively new technique to reduce the recurrence of occlusion after a balloon angioplasty procedure involves providing a stent at the revascularized site. A stent is a hollow tube, typically braided, that can be inserted into the vasculature of a patient in a compressed form. Once properly positioned at a desired site, the stent is expanded to hold the vessel open in an attempt to prevent restenosis. While this technique can help maintain blood flow past the site, it has been found that the occluding material often migrates through the interstices of the stent braid, and may again occlude the vessel. This phenomenon is sometimes referred to as interstitial hyperplasia.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as rotating cutters or ablaters, for example, to remove the occluding material. The rotating cutters may be particularly useful in removing certain vascular occlusions.

In operation, an atherectomy device is typically advanced over a guide wire placed in vivo until the device is positioned just proximal to the occluded site. A motor is used to rotate a driveshaft coupled to the device, and the device is moved through the occluded vessel. Frequently, an aspiration device is utilized in conjunction with the device to remove the loose particulate broken off by the device so that the particulate is not introduced into the body. Typically, a conventional aspiration device consists of a catheter in fluid communication with a vacuum source or negative pressure such as a vacuum pump or bottle. The catheter, generally surrounding the driveshaft, is advanced to the occlusion site over the guide wire to remove the loose particulate.

However, problems can occur when treating various vessels of the patient. For example, in saphenous vein grafts (SVG) and with stented vessels, the occluding material or gromous has a tendency to be more loosely organized and brittle, which makes the material friable. Therefore, in operation, conventional devices tend to break off large pieces of this material rather easily due to its morphology, instead of ablating it. These large particulate are then sucked into the mouth of the aspirating catheter, causing the loose particulate to become lodged in the mouth of the catheter. As a result, the occlusion site is presented with a lack of vacuum pressure that could hinder the aspiration process.

Therefore, there exists a need for an improved ablation burr system and process for removal of large, liberated particulate within an occluded blood vessel to overcome the deficiencies in the prior art.

SUMMARY OF THE INVENTION

An ablation system is provided to overcome the deficiencies in the prior art. The ablation system comprises an atherectomy device and an aspiration catheter, each routed to a position just proximal to a lesion within a patient's vessel to ablate and remove the lesion so that blood flow through the vessel is adequately restored.

In one embodiment of the invention, an ablation system includes a driveshaft, an ablation burr coupled to the driveshaft and an aspiration catheter. The aspiration catheter has a trap for collecting particles of occluding matter that are ablated by the burr.

In accordance with another aspect of the present invention, a mechanism is provided that cooperates with the trap on the aspiration catheter to clear collected particles from the trap.

In accordance with yet another aspect of the present invention, a system for ablating an occlusion in a patient's vessel comprises an ablation burr having a front surface and a rear surface, and being rotatable to ablate the occlusion. The system also comprises an aspiration catheter having proximal and distal ends. The catheter includes a lumen that extends longitudinally therethrough. The lumen forms an aspiration mouth at the distal end of the aspiration catheter, where the aspiration catheter includes a tapered inner surface defining a portion of the lumen.

In accordance with still another aspect of the present invention, a method is provided for ablating a lesion in a patient's vessel using an ablation burr system. An atherectomy burr is routed to a position just proximal to the lesion, the burr having a downwardly tapering rear surface. An aspiration catheter is routed to a position just proximal to the burr, the aspiration catheter having proximal and distal ends and including a lumen that extends longitudinally therethrough. The lumen forms an aspiration mouth at the distal end of the aspiration catheter, where the aspiration catheter includes a tapered inner surface defining a portion of the lumen. The burr is advanced distally through the lesion causing loose particulate to separate from the vessel wall. The loose particulate is aspirated with the aspiration catheter. The aspiration mouth of the aspiration catheter is cleared by pulling the burr proximally toward the aspiration catheter so that the burr can break down the loose particulate for removal by the catheter.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a side elevation view of an exemplary embodiment of an ablation burr system within an occluded vessel in accordance with aspects of the present invention;

FIG. 2 is a partial cross-sectional view of an exemplary embodiment of an atherectomy device shown in FIG. 1;

FIG. 3 is a partial cross-section view of an exemplary embodiment of an aspiration catheter shown in FIG. 1;

FIG. 4 is a cross-sectional view of the exemplary embodiment of the ablation burr system shown in FIG. 1 wherein the atherectomy device is advanced away from the aspiration catheter;

FIG. 5 is a cross-section view of an exemplary embodiment of the ablation burr system shown in FIG. 1 wherein the atherectomy device is pulled proximally toward and within the aspiration catheter;

FIG. 6 is a perspective view of an exemplary embodiment of the distal end portion of the aspiration catheter shown in FIG. 1;

FIG. 7 is an end view of an alternative embodiment of the aspiration catheter in accordance with aspects of the present invention;

FIG. 8 is a perspective view of a distal end portion of an alternative embodiment of the aspiration catheter illustrating a contoured inner tapered portion; and FIG. 9 is an end view of an alternative embodiment of the aspiration catheter illustrating a different cross-sectional geometry of the aspiration mouth.

DETAILED DESCRIPTION OF THE PREFERRED EMBODIMENT

FIG. 1 illustrates an exemplary embodiment of an ablation burr system 20 within an occluded vessel V, such as an SVG, having a lesion L in it. The ablation system 20 comprises an atherectomy device 22 and an aspiration catheter 24, each routed to a position just proximal to the lesion L to ablate and remove the lesion L so that the blood flow through the vessel V is adequately restored.

Referring now to FIG. 2, the atherectomy device 22 includes a flexible driveshaft 26 coupled to an ablation burr 28. The flexible driveshaft 26 has a lumen 30 extending therethrough to receive a guide wire 34, as shown. The driveshaft 26 is coupled at its proximal end to a source of rotational motion such as an electric motor or gas turbine (not shown) that rotates the driveshaft at high speeds, e.g., between 20,000 and 250,000 rpm. In operation, with reference to FIGS. 1 and 2, the guide wire 34 is percutaneously inserted through the vasculature of a patient, and past the site of the lesion L. The atherectomy device 22 is then routed to a point near the site of lesion L over the guide wire 34 by an advancer, not shown but well known in the art. A guide catheter 36, shown in FIGS. 4 and 5, may be used to assist in the positioning of both the guide wire 34 and the atherectomy device 22, also known in the art. Extending through the guide catheter 36 is the aspiration catheter or sheath 24 for aspirating loose particulate 40 that breaks off during ablation. The ablation burr 28, when rotated by the driveshaft 26, ablates a new lumen through the lesion L in order to permit blood to flow freely through the vessel V. The aspiration catheter 24, due to the presence of a vacuum or negative pressure, removes the loose particulate 40 from within the vessel.

Referring to the exemplary embodiment of the present invention shown in FIG. 2, the atherectomy device 22 of the ablation system 20 preferably comprises a flexible driveshaft 26 coupled to an ablation burr 28, wherein the flexible driveshaft 26 and the ablation burr 28 are disposed about a central axis. The ablation burr 28 is preferably constructed from a metallic material such as brass, and is shaped to have a generally concave front or leading surface 42 and a generally frusto-conical rear or trailing surface 44. In the embodiment shown, the concave front surface 42 extends from an inner circumferential rim or edge portion 46 at the distal tip of the burr 28 to a ridge or crest 48 disposed approximately at the midpoint of the burr 28. The frusto-conical rear surface 44 extends from an inner circumferential rim or edge portion 50 at the proximal tip of the burr 28 to the ridge 48. Accordingly, the ridge 48 has an outer diameter greater than either inner circumferential edge portions 46, 50.

As shown in FIG. 2, an axial socket 52 is disposed along the central axis and extends through the frusto-conical rear surface region of the burr 28 for receiving the end of the driveshaft 26. The ablation burr 28 further includes a guide wire lumen 54 concentric with but having a smaller diameter than the axial socket 52. The guide wire lumen 54 extends from the distal end of the axial socket 52, through the concave front surface 42, and terminates at the distal end of the ablation burr 28 so that the ablation burr 28 may be threaded over guide wire 34.

As indicated above, the front surface 42 of the burr is concave in cross section and is partially or totally covered with an abrasive material 58 such as diamond grit to ablate the lesion L when the burr is rotated. The frusto-conical shaped rear surface 44 of the burr is also totally or partially covered with an abrasive material 60 such as diamond grit, the purpose of which is discussed in more detail below. The abrasive material 58, 60, can be secured on the outer surfaces 42, 44, of the burr by any conventional method such as electro and/or electroless plating. A smooth or non-abrasive portion 62 of the burr having a non-abrasive surface is preferably formed between the abrasive material 58, 60, found at the distal end and proximal ends of the burr. The non-abrasive portion 62 preferably begins at a point of maximum diameter of the burr and continues proximally along a portion of the rear surface 44 of the burr in order to reduce irritation at the vessel walls.

Referring now to FIG. 3, the aspiration catheter 24 is routed to a position just proximal to the site of the lesion adjacent to the ablation burr so that the catheter 24 can aspirate or remove the loose particulate that might be broken off by the ablation burr. The aspiration catheter 24 is in fluid communication with a vacuum source (not shown) such as a vacuum pump or bottle as is know in the art. It will be appreciated that other devices (not shown) may be used in conjunction with vacuum source such as a blood filter and pump to return the aspirated blood to the patient. The aspiration catheter 24 has an elongate body of a generally cylindrical shape and includes a centrally located lumen 80 so that the driveshaft 26 can extend therethrough. The lumen 80 also provides an conduit for loose particulate to be removed from the vessel.

As shown in FIGS. 3 and 6, the centrally located lumen 80 is concentric with the driveshaft 26 and is separated into two portions having different inner geometries. The two portions consist of a generally constant inner diameter proximal portion 82 and a generally conical distal portion 84. The distal portion 84 of the lumen 80 is positioned approximately at the distal end of the catheter 24 and defines an aspiration mouth 86 for receiving the loose particulate as vacuum or negative pressure is supplied to the catheter 24 via the centrally located lumen 80. The distal portion 84 narrows from the distal end of the catheter 24 toward the proximal end of the catheter 24 in an inwardly tapered manner to form a generally conical inner surface 90. The taper of the inner surface 90 of the catheter 24 generally corresponds to the taper of the rear surface 44 of the ablation burr 28, as best shown in FIGS. 4 and 5, so that the ablation burr may be pulled back into the distal portion 84 of the lumen 80 during operation of the ablation burr system 20.

In the embodiment shown, the diameter of the aspiration mouth 86 is substantially equal to the diameter formed by the generally constant inner diameter proximal portion 82. The constant inner diameter portion 82 extends from the proximal end of the aspiration catheter 24 toward the distal end of the aspiration catheter 24. A small, generally cylindrical lumen 88 having a substantially constant diameter may connect the proximal and distal portions 82, 84 to provide an integral lumen 80 extending through the catheter 24.

The inner surface 90 of the aspiration catheter 24 may be suitably contoured or textured to help grab or retain the loose particulate within the catheter 24. For example, a plurality of elongate ribs or splines 92 may be positioned around the inner surface 90 of the aspiration catheter 24 to hold the loose particulate, as shown in FIGS. 7 and 8. Alternatively, the aspiration mouth 86 may have a different cross-sectional geometry, such as a star-shaped opening shown in FIG. 9 which can act as a filter to collect the loose particulate at or near the mouth 86 of the aspiration catheter 24. While the embodiments shown are exemplary of suggested configurations, it will be readily apparent to those skilled in the art that any one of a variety of suitable inner surface textures or aspiration mouth geometric openings are within the scope of the present invention.

The operation of the ablation system constructed in accordance with aspects of the present invention will now be described with reference to FIGS. 1, 4 and 5. The ablation burr 28 is routed over the guide wire 34 to the site of the lesion L. The aspiration catheter 24 is then routed to just proximal the ablation burr 28. The ablation burr 28 is spun up to speed by the driveshaft 26, which is rotated by rotational means such as a gas turbine or an electric motor. As the burr 28 is rotated, the burr 28 is advanced through the lesion L by the advancer (not shown), whereby the abrasive 58 positioned on the front surface 42 of the burr 28 ablates the lesion L. During the ablation procedure, loose particulate 40 that was not completely ablated is detached from the vessel wall and remains suspended within the blood of the vessel V. A slight vacuum present at the mouth 86 of the aspiration catheter 24 pulls the loose particulate 40 within the mouth 86 of the catheter 24. Due to the presence of the frusto-conical inner surface 90 within the mouth 86 of the catheter 24, large pieces of the loose particulate 40 are trapped between the driveshaft 26 and the frusto-conical inner surface 90 of the aspiration catheter 24.

After the lesion L is fully ablated or when the physician notices a drop in aspiration pressure, the ablation burr 28 may be pulled back by the advancer toward the mouth 86 of the aspiration catheter 24. Due to the tapered rear surface 44 of the ablation burr 28, the ablation burr 28 may be pulled into the mouth 86 of the aspiration catheter 24. The ablation burr 28, still rotating via the driveshaft 26, ablates or breaks up the loose particulate 40 trapped within the aspiration catheter 24 due to the abrasive material 60 disposed on the rear surface 44 of the ablation burr 28. The loose particulate 40 is broken up into suitable dimensioned pieces 94 by the ablation burr 28 so that it may be removed by the aspiration catheter 24.

While the preferred embodiment of the invention has been illustrated and described, it will be appreciated that various changes can be made therein without departing from the scope of the invention. For example, the aspiration catheter need not have a frusto-conically-shaped lumen at its distal end. Other shapes that both trap ablated particles between the lumen walls and the driveshaft as well as cooperate with the rear of the burr to clear the catheter could be used. Such shapes could be cylindrical, ovoidal, etc. Similarly, the rear surface of the ablation burr could include a number of blades that fit within the distal end of the aspiration catheter to clear trapped particles. If the catheter has a star-shaped or slotted lumen, as shown in FIGS. 7–9, then the rear surface of the burr may have a corresponding shape to clear the entrance to the catheter. Such shapes may be like a key such that they fit within the catheter when the burr is not rotating. It is therefore intended that the scope of the invention be determined from the following claims and equivalents thereof.

The embodiments of the invention in which an exclusive property or privilege is claimed are defined as follows:

1. An aspiration catheter for use in an ablation system, the ablation system operable for removing lesion material from a patient's vasculature, comprising:

an elongate body having proximal and distal ends and including inner side walls that define a lumen and a filter section at its distal end;

wherein said lumen has a first cross-sectional area and said filter section has a distal opening with a second cross-section area at said distal end of said elongate body and a proximal opening with a third cross-sectional area positioned proximal to said distal opening, wherein said cross-sectional area of said proximal opening of said filter section is smaller than said cross-sectional area of said lumen and said cross-sectional area of said distal end of said filter section.

2. The catheter of claim 1, wherein said inner walls of said filter section are contoured.

3. The catheter of claim 1, wherein said contoured side walls of said filter section include longitudinally extending splines.

4. The catheter of claim 1, wherein said aspiration mouth forms a star shaped opening.

5. A method for ablating a lesion in a patient's vessel using an ablation burr system comprising:

routing an atherectomy burr that is connected to a driveshaft over a guidewire to a position just proximate to said lesion, said burr having a proximal surface;

routing an aspiration catheter over the driveshaft to a position just proximate to said burr, said aspiration catheter having proximal and distal ends and including a lumen extending longitudinally therethrough, said lumen forming an aspiration mouth at said distal end of said aspiration catheter, wherein said aspiration catheter includes a filter section defining a portion of said lumen that cooperates with said proximal surface of said burr;

rotating and advancing said burr distally through said lesion causing loose lesion particulate to separate from the vessel wall;

aspirating said loose lesion particulate with said aspiration catheter;

filtering at least some of said loose lesion particulate by trapping said loose lesion particulate in said filter section; and clearing said filter section from said trapped lesion particulate by moving said rotating burr toward said aspiration catheter and into engagement with said trapped lesion particulate so that said proximal surface of the burr breaks down said trapped lesion particulate for removal by said catheter.

6. The method of claim 5, wherein clearing said aspiration mouth of said aspiration catheter occurs during the atherectomy process when a loss in aspiration pressure is determined.

7. The method of claim 5, wherein clearing said aspiration mouth of said aspiration catheter occurs after the lesion has been fully removed and the blood flow through the vessel has been restored.

* * * * *

UNITED STATES PATENT AND TRADEMARK OFFICE
CERTIFICATE OF CORRECTION

PATENT NO.   : 6,632,230 B2
DATED        : October 14, 2003
INVENTOR(S)  : R.L. Barry It is certified that error appears in the above-identified patent and that said Letters Patent is hereby corrected as shown below:

<u>Column 7,</u>
Line 6, "cross-section" should read -- cross-sectional --

<u>Column 8,</u>
Line 7, "lesion causing" should read -- lesion, causing --

Signed and Sealed this

Sixteenth Day of March, 2004

JON W. DUDAS
*Acting Director of the United States Patent and Trademark Office*